United States Patent
Sealfon

(10) Patent No.: US 12,409,308 B2
(45) Date of Patent: Sep. 9, 2025

(54) MANIFOLD FOR INFUSION SYSTEM

(71) Applicant: INNOVATIVE HEALTH SCIENCES, LLC, Chester, NY (US)

(72) Inventor: Andrew Sealfon, Chester, NY (US)

( * ) Notice: Subject to any disclaimer, the term of this patent is extended or adjusted under 35 U.S.C. 154(b) by 0 days.

(21) Appl. No.: 18/306,477

(22) Filed: Apr. 25, 2023

(65) Prior Publication Data

US 2023/0338723 A1 Oct. 26, 2023

Related U.S. Application Data

(60) Provisional application No. 63/334,961, filed on Apr. 26, 2022.

(51) Int. Cl.
| | | |
|---|---|---|
| *A61M 39/10* | (2006.01) | |
| *A61M 5/14* | (2006.01) | |
| *A61M 39/24* | (2006.01) | |

(52) U.S. Cl.
CPC .............. *A61M 39/10* (2013.01); *A61M 5/14* (2013.01); *A61M 39/24* (2013.01); *A61M 2005/1401* (2013.01); *A61M 2039/1083* (2013.01); *A61M 2039/1088* (2013.01)

(58) Field of Classification Search
CPC .............. A61M 39/223; A61M 39/225; A61M 2209/045; A61M 5/1408
See application file for complete search history.

(56) References Cited

U.S. PATENT DOCUMENTS

| | | | |
|---|---|---|---|
| 2004/0221904 A1* | 11/2004 | Usher | A61M 39/24 137/837 |
| 2009/0198217 A1* | 8/2009 | Thorne, Jr. | A61M 5/162 604/83 |
| 2016/0346472 A1* | 12/2016 | Mitchell | A61M 39/1011 |
| 2020/0338260 A1* | 10/2020 | Kim | A61M 39/24 |

* cited by examiner

*Primary Examiner* — Courtney B Fredrickson
(74) *Attorney, Agent, or Firm* — Carlson, Caspers, Vandenburgh & Lindquist, P.A.

(57) ABSTRACT

An infusion system includes a primary delivery device, a secondary delivery device, an ancillary device, and a manifold. The manifold includes a primary connection port fluidly coupled with the primary delivery device. A delivery connection port in fluid communication with the primary connection port is fluidly coupled with the ancillary device. A secondary connection port fluidly coupled with the secondary delivery device is in fluid communication with the primary connection port. The primary connection port is operable to permit bidirectional flow so that fluid flows from the primary delivery device through the primary connection port and through the delivery connection port to the ancillary device, and from the secondary delivery device through the secondary connection port and through the primary connection port to be received by the primary delivery device.

12 Claims, 4 Drawing Sheets

MANIFOLD FOR INFUSION SYSTEM

CROSS-REFERENCE TO RELATED APPLICATION

This application claims priority to U.S. Provisional Patent Application No. 63/334,961, filed in the U.S. Patent and Trademark Office on Apr. 26, 2022, all of which is incorporated herein by reference in its entirety for all purposes.

FIELD

The present disclosure relates generally to infusion systems and for transferring fluid between fluid reservoirs or other vessels.

BACKGROUND

Infusion systems for the delivery of liquid pharmaceuticals are widely used and relied upon by patients and care givers alike. In conventional systems, a syringe or other fluid delivery device is connected to medical tubing such as an infusion set for fluid (for example medication) administration to a patient. Infusion systems often administer medicine intravenously or subcutaneously. Infusion systems often deliver specialty medications for rare diseases and chronic illnesses for conditions or diseases that do not respond to other treatment pathways such as oral medication. Some examples include bacterial or fungal infections, cancers, migraines, chronic pain, osteoporosis, heart failure, and autoimmune diseases. The medical infusion industry is ever growing and immersive in technologies providing infusion patients countless therapies for many conditions and disease states.

An infusion system typically consists of an infusion driving device (for example a pump), a reservoir for a delivery device (for example a syringe), a fluid (for example drug or medication), and ancillary administration devices that are used by healthcare professionals, caregivers, and patients. During an infusion in which a syringe-based infusion system is used, a primary syringe is either filled by the user or is already prefilled with medicine upon receipt and operated with an infusion pump. The infusion pump actuates the syringe to dispense the drug out of the syringe to an ancillary administration device, such as a needle set including tubes and one or more needles to deliver the medicine to the patient. Typically, the syringe is directly connected to the infusion sets through medical connections, such as luer connections.

BRIEF DESCRIPTION OF THE DRAWINGS

Implementations of the present technology will now be described, by way of example only, with reference to the attached figures, wherein.

DETAILED DESCRIPTION

Figure 1:
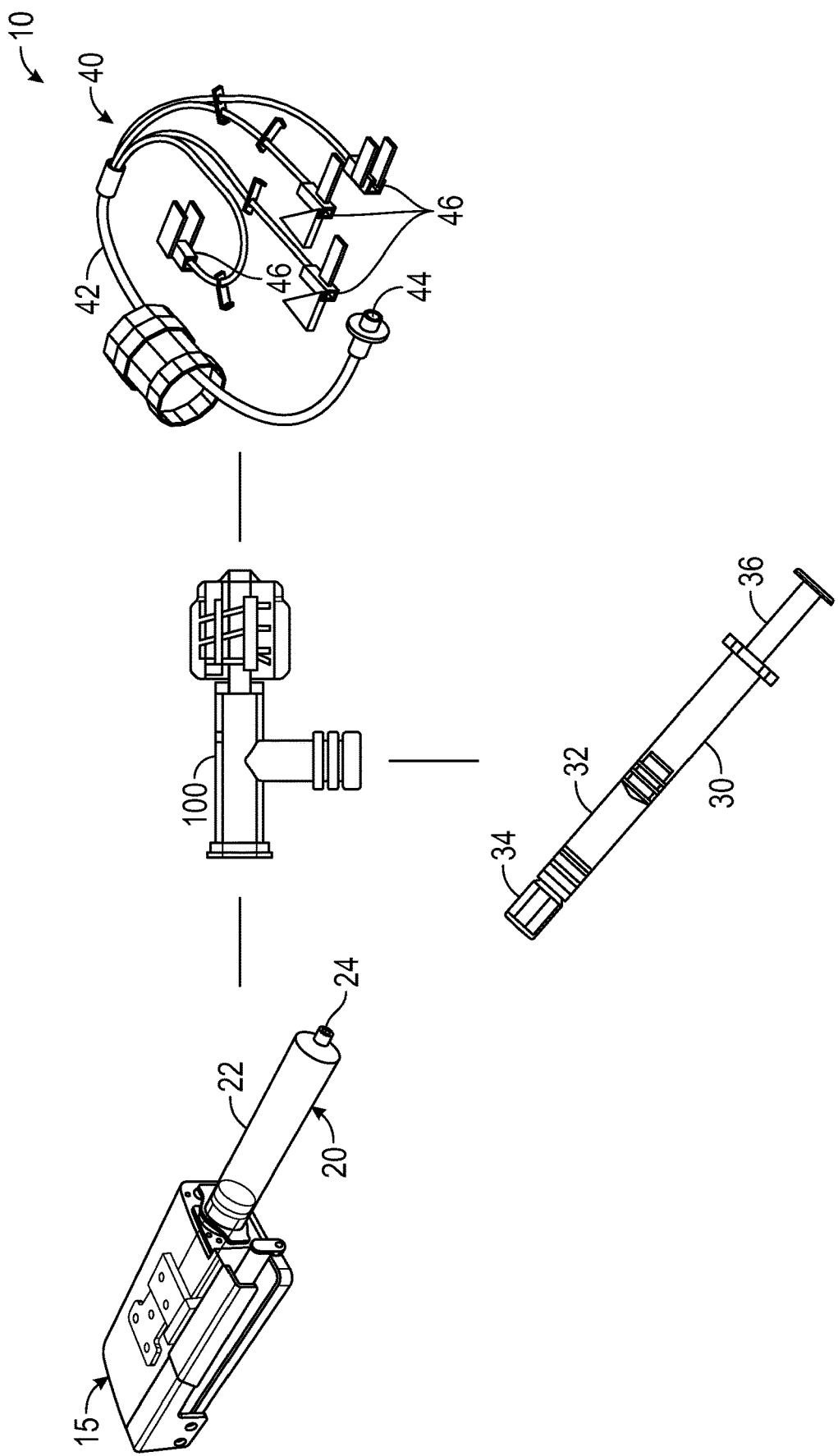
FIG. 1 is an infusion system.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout this disclosure will now be presented. The term "coupled" is defined as connected, whether directly or indirectly through intervening components, and is not necessarily limited to physical connections. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "about" means reasonably close to the particular value. For example, about does not require the exact measurement specified and can be reasonably close. As used herein, the word "about" can include the exact number. The term "near" as used herein is within a short distance from the particular mentioned object. The term "near" can include abutting as well as relatively small distance beyond abutting. The terms "comprising," "including" and "having" are used interchangeably in this disclosure. The terms "comprising," "including" and "having" mean to include, but not necessarily be limited to the things so described.

In some instances, infusions may require only a single syringe with a relatively small volume of drug (e.g., 50 milliliters) to deliver the therapeutic effect. In some instances, infusion therapies may require a larger drug volume that cannot fit into a single syringe. Delivering additional drug volume requires more syringes to complete the infusion therapy.

For example, low-volume syringe infusion systems conventionally use syringes that can hold volumes up to 60 milliliters (mL). Patients undergoing large volume infusions, e.g., 300 mL volumes, are often provided within 5 syringes (or syringe refills), each holding 60 mL of the drug. The first syringe is fitted to the ancillary device, such as a needle set, and the syringe is then placed within the infusion driving device (e.g., a pump). After the first syringe with 60 mL of drug has been administered, the second volume of the drug in the second syringe needs to be introduced. To do this, conventionally, the empty first syringe must be removed from the pump, and the infusion set must be disconnected from the first syringe. In many intravenous administrations the infusion set must also be disconnected from an indwelling catheter in the patient. The infusion set must then be re-connected to the next syringe, and the syringe must then be inserted back into the infusion pump. This process is often termed "the syringe replacement method" and is associated with introducing the potential for contamination and infection.

Alternatively, the primary syringe can conventionally be refilled with an additional volume of the medicine to re-supply the infusion system with the additional drug volume needed. This is termed a "syringe tip-to-tip" transfer. In this case, after the initial drug volume is dispensed, the infusion set is disconnected from the primary syringe, the secondary syringe is connected to the primary syringe with a transfer device such as a female-to-female luer adapter, and the primary syringe is refilled with the drug from the secondary syringe. Once the primary syringe is refilled, the secondary syringe is disconnected, the primary syringe is reconnected to the infusion set, and the treatment starts again. The tip-to-tip transfer method is advantageous in cases where only the primary syringe is compatible for use with the infusion pump, but the secondary syringe and additional syringes afterwards are not.

Both conventional syringe replacement and tip-to-tip transfer options require excessive labor and attention to care, and they introduce a source of sterility-contamination each time the infusion needle set connection or other ancillary device connections are handled. The user replenishing the infusion fluids needs to carefully perform the steps without introducing contamination to the infusion. In both methods, the infusion needle set connection is altered and creates a sterility risk and a potential source of infection for the patient. Also, to replenish infusion fluids that require multiple syringes, users must repeat the syringe replacement or tip-to-tip transfer steps several times, which can become tedious, tiresome, inefficient, and significantly increase the risk of contamination.

To address versatility, infusion drugs can be prepared and distributed within prefilled syringes. The prefilled syringe sector of the industry lacks universal infusion systems dedicated to accommodating all sizes of prefilled syringes. Even syringes from the same brand are not standardized.

While electric or smart infusion systems can be used to detect automatically the type of syringe used, the syringe data library must be created or updated for every new or changed syringe. Further, electric and smart infusion systems are prone to user input errors that can cause patients to receive an incorrect infusion therapy. Electric and smart infusion systems require a power supply, are expensive, require constant upkeep, provide false alarms, and are not always available or accessible. For example, for a medical military application, users may experience long periods of time when no power is available, but medical treatment is urgently needed, making electric and smart infusion systems not a viable option.

A mechanical, nonelectrical infusion system can provide a great deal of versatility for prefilled syringes as they are inexpensive, require little to no maintenance, require no power, are portable, and can be used worldwide. The issue with a mechanical infusion system, such as constant pressure systems, when used for prefilled syringes, is that their designs are typically dedicated for a certain size syringe.

Infusion systems may be intended to be used with specific syringes. The system can be modified to accommodate different dimensions of various prefilled syringes, but the more prefilled syringes to be accommodated, the more complex the design of the infusion system.

Instead of accommodating a countless range of prefilled syringe volumes and sizes, infusion systems could be adapted to provide cardinal drug volumes. For example, if prefilled syringes are offered in sizes of 5 mL, 10 mL, 20 mL, and 50 mL volumes, the design of the infusion system may be too complex to accommodate all of the different syringes. An alternative solution may be to design the infusion system for the 10 mL and 50 mL prefilled syringe volumes, and the manufacturer can prepare and fill the 5 mL and 10 mL volumes of the drug in a 10 mL prefilled syringe. Similarly, 20 mL and 50 mL volumes can be prepared and filled in a 50 mL syringe. This provides a plausible solution but limits the ability to directly use specific prefilled syringes, such as the 5 mL and 20 mL volumes.

A mechanical infusion system dedicated to certain volumes can be limited to accommodating only the prefilled syringes of a select brand or manufacturer. Enabling the use of more and different prefilled syringes requires a more complex design or several dedicated infusion systems. This limits the versatility in providing a "one size fits all" type of infusion system.

Infusion systems dedicated to certain syringe types or certain fluid reservoirs require that specific syringe or reservoir for the infusion to function as intended. The recent crippling of the global supply chain has left many raw materials and finished goods inaccessible. For example, a user may have a working infusion system but not the intended syringe due to supply restrictions. As such, they are unable to perform the infusion.

With multi-syringe infusions, more than one prefilled syringe is required. Extending the example of the 5 mL, 10 mL, 20 mL, and 50 mL prefilled syringes mentioned prior, to create a 20% concentration immunoglobulins (IgG), 1 gram of the drug is needed for every 5 mL. If a patient requires 7 grams of the drug, they will need a 5 mL (1 g), a 10 mL (2 g), and a 20 mL (4 g) mL prefilled syringe. This underscores the problem for multi-syringe infusions where syringe and infusion set connections are handled multiple times and become a source of contamination and possible infection.

As another 20% IgG drug example, to deliver 12 g of a drug, 60 mL is required. Using the tip-to-tip syringe transfer method, 60 mL of the drug can be transferred from the prefilled syringes to a single syringe compatible with a mechanical infusion system. However, some patients require more than 12 g of the drug and therefore more than 60 mL, which will require refilling or replacing the primary syringe, again creating the multi-syringe handling and contamination problem.

Further, different concentrations of IgG drugs exist, such as 16.5% concentrations. To deliver the same 12 g of IgG, a 16.5% concentration of IgG drug requires 72 mL, which will require refilling the primary syringe again creating syringe and infusion set handling issues and sources of contamination.

Many drugs are packaged in pre-existing prefilled syringes that are fixed to a particular volume and thus the number of grams required to maintain the drug concentration is expressed as a decimal instead of a whole number. For example, using the 5 mL, 10 mL, 20 mL, and 50 mL prefilled syringe example with 20% concentration IgG drugs, whole numbers of 1 g, 2 g, 4 g and 10 grams of the drug are used to achieve the drug concentrations, respectively. When a 16.5% concentration IgG drug is placed within the same prefilled volumes of 5 mL, 10 mL, 20 mL, and 50 mL, the number of grams of the drug required to maintain the 16.5% concentration are 0.825 g, 1.65 g, 3.3 g and 8.25 grams, respectively. A patient requiring 12 grams of 16.5% IgG drug could never receive the exact amount of the drug. The amount would be close. However, it requires performing math with decimals, which is more likely prone to user error, and may not deliver the full therapeutic effect.

As many patients are prescribed a monthly dosage of drug, using only prefilled syringes during that month may require different sizes of prefilled syringes or rotating monthly delivery intervals to achieve the required dosage. In instances where a patient may be rotated on more than one size of prefilled syringes or where the patient is required to change their weekly schedule to infuse on different days, they may better approximate their prescribed monthly dosage, but this also may cause confusion and user error when maintaining and reporting the patient's infusion schedule and dosage.

To provide whole number grams of the required drug to patients, some drug manufacturers offer prefilled vials. For example, the 16.5% concentration IgG is offered in 6 mL, 10 mL, 12 mL, 20 mL, 24 mL, and 48 mL prefilled vials where the vials contain 1 g, 2 g, 4 g, and 8 grams of the drug, respectively. If the patient required 12 grams of drug, they could now use a 24 mL prefilled vial and a 48 mL prefilled vial, in comparison to using 20 mL and 50 mL prefilled syringes in which they would only receive 11.55 grams of the drug.

Further, if a patient had limited accessibility to certain vials or prefilled syringes, they could combine together the drug from both into a syringe to achieve the desired amount of drug. Through this, any combination of drug dosage can be achieved. However, using a prefilled vial requires the use of additional equipment and labor. For example, to withdraw a drug from both a prefilled vial and a prefilled syringe into a primary syringe compatible with the infusion system, the user must use a transfer device, such as a vial spike, to withdraw the drug from the vial into the primary syringe. Then, the spike must be removed, and a syringe tip-to-tip transfer device, such as a dual female luer connector, needs to be attached to now withdraw the drug from the prefilled syringe into the primary syringe.

This method, though tedious, seems plausible, but additional drug volumes beyond the capacity of the primary syringe require additional syringe refilling in which the sterile connection between the infusion set must be broken. This re-introduces the handling and contamination concerns mentioned above.

Further, the methods and delivery devices disclosed herein are not limited to vials and syringes but can extend to other drug reservoirs, such as bags or chambers, etc. In the event multiple types of reservoirs are used, conventional technologies and techniques for drug transfers while maintaining a close-sterile system cannot provide a solution without causing complications to the user.

The systems and methods disclosed herein provide a technical solution to foregoing problems with conventional infusion systems, and provide for increased safety, efficiency, and patient care when compared to conventional systems and methods for delivering infusion therapy medicine to a patient.

Turning to FIG. 1, an infusion system 10 can include an infusion driving device 15, a primary delivery device 20, a secondary delivery device 30, and an ancillary device 40.

The infusion driving device 15 can include a pump which is operable to receive the primary delivery device 20.

The primary delivery device 20 can include a primary reservoir 22 operable to receive and store fluid (e.g., drug, infusion fluid, etc.) and a tip 24 through which the fluid passes into and/or out of the primary reservoir 22 of the primary delivery device 20. The infusion driving device 15 can be operable to cause the primary delivery device 20 to dispense the fluid in the primary reservoir 22. In at least one example, the primary delivery device 20 includes a syringe. In some examples, the primary delivery device 20 can include a 50 milliliter syringe. In at least one example, the primary delivery device 20 includes a bag, a chamber, and or any other suitable component or mechanism to receive and dispense fluid. In at least one example, the infusion driving device 15 can impart a force or a pressure on a plunger of the primary delivery device 20 to push the fluid out of the primary reservoir 22 of the primary delivery device 20 through the tip 24.

The secondary delivery device 30 can include a secondary reservoir 32 operable to receive and store fluid (e.g., drug, infusion fluid, etc.) and a tip 34 through which the fluid passes into and/or out of the secondary reservoir 32. The secondary delivery device 30 can be operable to dispense the fluid in the secondary reservoir 32. In at least one example, the secondary delivery device 30 includes a syringe. In some examples, the secondary delivery device 30 can include a 10, 15, 20, 30, 40, 50, etc. milliliter syringe. In at least one example, the secondary delivery device 30 includes a bag, a chamber, and or any other suitable component or mechanism to receive and dispense fluid. In at least one example, a user and/or a device can impart a force or a pressure on a plunger 36 of the secondary delivery device 30 to push the fluid out of the secondary reservoir 32 of the secondary delivery device 30 through the tip 34. In at least one example, the secondary delivery device 30 can include a pre-filled reservoir (e.g., a pre-filled syringe and/or a pre-filled vial).

The ancillary device 40 can include an infusion needle set. The infusion needle set can be operable to deliver the fluid from the primary delivery device 20 to a patient. The infusion needle set can include a fitting 44 operable to be in fluid communication with the primary delivery device 20 to receive the fluid. The fluid can then flow from the fitting 44 into one or more channels 42 which are fluidly coupled with corresponding one or more needles 46. The needles 46 can be inserted into the patient and deliver the fluid to the patient through the needles 46.

A manifold 100 can be operable to be fluidly coupled with the primary delivery device 20, the secondary delivery device 30, and the ancillary device 40. The manifold 100 can be operable to permit and/or control fluid flow between the primary delivery device 20, the secondary delivery device 30, and the ancillary device 40. With the manifold 100, the secondary delivery device 30 can provide fluid (the same fluid as in the primary delivery device 20 and/or a different fluid) to be received in the primary reservoir 22 of the primary delivery device 20 while still permitting fluid to flow from the primary reservoir 22 of the primary delivery device 20 to the ancillary device 40.

Figure 2:
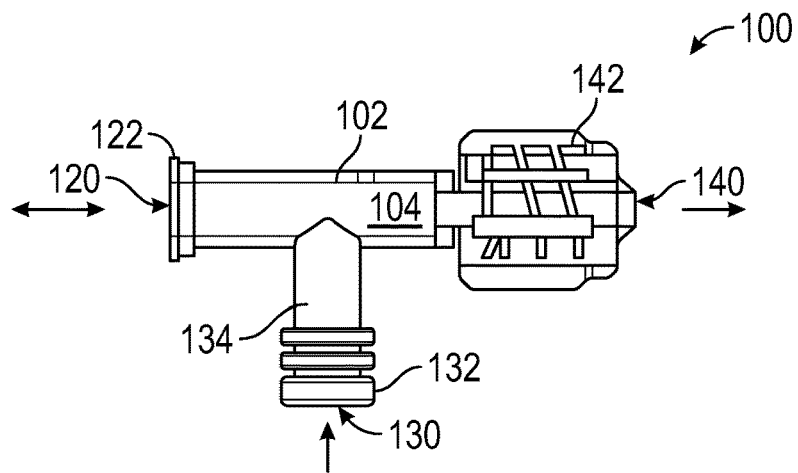
FIG. 2 is a manifold for the infusion system.

Referring to FIG. 2, the manifold 100 can include a body 102 that forms a primary channel 104 that fluidly connects a primary connection port 120 with a delivery connection port 140. A secondary extension 134 can extend from the primary channel 104 to fluidly connect a secondary connection port 130 with the primary connection port 120. The secondary extension 134 can be in fluid communication with the primary channel 104 such that fluid can flow from the secondary connection port 130 through the secondary extension 134 to the primary channel 104 and the primary connection port 120.

The primary connection port 120 can be operable to be fluidly coupled with the primary delivery device 20. In at least one example, the primary connection port 120 can include a luer connector 122 operable to receive the tip 24 of the primary delivery device 20. For example, when the primary delivery device 20 includes a syringe, the tip 24 can include a male luer fitting. The luer connector 122 of the primary connection port 120 can include a female luer connector 122 operable to receive the male luer fitting of the tip 24 of the primary delivery device 20. In some examples, the luer connector 122 of the primary connection port 120 can include a male luer connector 122 operable to be received by a female luer fitting of the primary delivery device 20.

The delivery connection port 140 can be operable to be in fluid communication with the primary connection port 120. The delivery connection port 140 can be operable to be fluidly coupled with the ancillary device 40. Accordingly, the fluid from the primary delivery device 20 can be operable to flow from the primary reservoir 22 of the primary delivery device 20 through the primary connection port 120 and through the delivery connection port 140 to the ancillary device 40 to delivery the fluid to the patient.

In at least one example, the delivery connection port 140 can include a luer connector 142 operable to receive the fitting 44 of the ancillary device 40. For example, the fitting 44 for an ancillary device 40 that includes a infusion needle set can include a female luer fitting. The luer connector 142 of the delivery connection port 140 can include a male luer connector 142 operable to receive the female luer fitting 44 of the ancillary device 40. In some examples, the luer connector 142 of the delivery connection port 140 can include a female luer connector 142 operable to be received by a male luer fitting 44 of the ancillary device 40.

In at least one example, the delivery connection port 140 can be a luer-activated connector, sterile connector, clave connector, or needle-free connector used to maintain sterility when the delivery connection port 140 is vacant of an ancillary device 40.

A secondary connection port 130 can be operable to be fluidly coupled with the secondary delivery device 30. The secondary connection port 130 can be in fluid communication with the primary connection port 120. The fluid from the secondary delivery device 30 can flow from the secondary reservoir 32 through the secondary connection port 130 and through the primary connection port 120 to be received by the primary reservoir 22 of the primary delivery device 20. Accordingly, the secondary delivery device 30 can provide an a second infusion fluid contained in the secondary reservoir 32 of the secondary delivery device 30 and/or additional fluid volume of a first infusion fluid that was contained in the primary reservoir 22 of the primary delivery device 20 to the primary delivery device 20 which can then be delivered to the patient via the ancillary device 40 while also maintaining the delivery connector port 40 for the ancillary device 40. In this way, the infusion can be replenished with the drug without breaking the sterile connection to the infusion needle set 40 and thus greatly reduce the risk of contamination and infection.

In at least one example, the secondary connection port 130 can include a luer connector 132 operable to receive the tip 34 of the secondary delivery device 30. For example, when the secondary delivery device 30 includes a syringe, the tip 34 can include a male luer fitting. The luer connector 132 of the secondary connection port 130 can include a female luer connector 132 operable to receive the male luer fitting of the tip 34 of the secondary delivery device 30. In some examples, the luer connector 132 of the secondary connection port 130 can include a male luer connector 132 operable to be received by a female luer fitting of the secondary delivery device 30.

In at least one example, the secondary connection port 130 can be a luer-activated connector, sterile connector, clave connector, or needle-free connector used to maintain sterility when the secondary connection port 130 is vacant of a secondary delivery device 30. In some examples, other fluid receiving connectors such as spikes, for example can be used to receive infusion fluids from bags or vials.

In at least one example, the secondary connection port 130 can be operable to permit unidirectional flow from the secondary delivery device 30 to the primary connection port 120 to prevent fluid to flow into the secondary delivery device 30 when the fluid is being delivered from the primary delivery device 20 to the ancillary device 40. In at least one example, the secondary connection port 130 can include a check valve. For example, the primary delivery device 20 is operable to deliver the second infusion fluid (which may be the additional volume of the first infusion fluid) to the ancillary device 40 by causing the second infusion fluid to flow from the primary delivery device 20 through the primary connection port 120 and through the delivery connection port 140 to the ancillary device 40 while the second infusion fluid is prevented from flowing through the secondary connection port 130.

In at least one example, the delivery connection port 140 can be operable to permit unidirectional flow from the primary connection port 120 to the ancillary device 40 to prevent fluid from the patient to flow back into the manifold 100. In at least one example, the delivery connection port 140 can include a check valve. In at least one example, the second infusion fluid (which may be the additional volume of the first infusion fluid) is operable to flow from the second connection port 130 to the primary delivery device 20 via the primary connection port 20 while the second infusion fluid and/or the additional volume of the first infusion fluid is prevented from flowing through the delivery connection port 40.

The primary connection port 120 is operable to permit bidirectional flow so that fluid is operable to flow: (1) from the primary delivery device 20 through the primary connection port 120 and through the delivery connection port 140 to the ancillary device 40, and (2) from the secondary delivery device 30 through the secondary connection port 130 and through the primary connection port 120 to be received by the primary delivery device 20. Accordingly, with the manifold 100, the fluid for the infusion can be delivered to the patient while also being replenished in the primary delivery device 20 with the secondary delivery device 30 without breaking the sterile connection to the ancillary device 40 and thus greatly reduce risk of contamination and infection. None of the components (the primary delivery device 20, the secondary delivery device 30, and/or the ancillary device 40) need to be removed from the manifold 100 or separately handled to deliver the fluid and also replenish with additional fluid.

To fill or replenish the primary delivery device 20, a user such as a clinician, patient or caregiver can connect the manifold 100 to the primary delivery device 20 (e.g., syringe) via the primary connection port 120 prior to starting the infusion. The user can connect the secondary delivery device 30 (e.g., syringe) to the manifold 100 via the secondary connection port 130. Also, the user can connect the ancillary device 40 (e.g., the infusion needle set) to the manifold 100 via the delivery connection port 140. The user can then deliver fluid from the primary delivery device 20, for example with the infusion driving device 15, to the patient via the ancillary device 40, and the user can refill the primary delivery device 20 with infusion fluid from the secondary delivery device 30. As the primary delivery device 20 exhibits less fluidic resistance than the ancillary device 40, the fluid from the secondary delivery device 30 fills the primary reservoir 22 of the primary delivery device 20.

The secondary delivery device 30 (e.g., syringe) can remain connected as the primary delivery device 20 redispenses the fluid because the secondary connection port 130 is a unidirectional connection port (e.g., Luer lock) connected to the secondary delivery device 30. For example, the secondary connection port 130 can act as check valve permitting flow in a single direction. The refilling process can be repeated for additional syringes. Compared to conventional techniques and systems, this process involves fewer user movements, and the primary delivery device 20 does not need to be removed from the infusion driving device 15, which may also lead to less interaction with the infusion driving device 15 and overall, less labor. Accordingly, the systems and methods disclosed herein reduce risks of contamination and infection.

In at least one example, the manifold 100 can be retrofit to conventional infusion systems 10 without requiring modification to the infusion systems 10. The manifold 100 can enable infusion systems 10 to use their native reservoir, such as a syringe, by using the secondary connector port 130 to transfer a pre-filled secondary delivery device 30 (e.g., syringe) to fill or replenish an empty primary delivery device 20 (e.g., syringe). Many infusion fluid reservoirs such as (prefilled) syringes, (prefilled) chambers, (prefilled) bags, (prefilled) vials, and other (prefilled) vessels share the same standard luer connectors, so many different types of reservoirs can be used with the manifold 100 to fill refill the primary reservoir 22 of the primary delivery device 20, regardless of the size or volume of the primary reservoir 22 of the primary delivery device 20. Multiple numbers and varying volumes of secondary delivery devices 30 can be used consecutively to fill or refill the primary delivery device 20.

While the manifold 100 disclosed herein discusses three connection ports (primary connection port 120, secondary connection port 130, and delivery connection port 140), in other examples, the manifold 100 can include more than three connection ports, where connection ports in excess of the three discussed herein can be used to attach additional syringes and/or reservoirs simultaneously. For example, four additional connection ports can be incorporated in the manifold 100, so four additional delivery devices can be attached simultaneously, where each additional connection port is a unidirectional flow connector port to allow only flow out of the additional delivery devices. In at least one example, the manifold 100 can be made of rigid or semi-rigid materials, such as plastics, including polycarbonate. In some examples, the manifold 100 can be made of flexible soft materials to avoid stress-cracking and leaking as a result of the weight of the delivery devices (e.g., the primary delivery device 120 and the secondary delivery device 130). In at least one example, the manifold 100 can be fitted and manufactured with support structures, such as feet, to support the weight of the delivery devices. In at least one example, the manifold 100 can be fitted and manufactured with support stands to hold delivery devices for ease of use and to help prevent air from entering the infusion fluid path. In at least one example, the connection ports can be fitted with mating caps to maintain sterility prior to use. In at least one example, the additional connection ports can allow additional and different delivery devices to be used, simultaneously, such as when different drugs need to be administered.

Excluding the dimensions of caps, in some examples, the manifold 100 can be designed and manufactured not exceed a maximum length of 1.50 inches. In some examples, the manifold 100 can be designed and manufactured not to exceed a maximum internal diameter of 0.20 inches. These dimensions lower the residual volume of the fluid that may remain in the manifold 100 after the infusion is complete (for example, the residual volume of the drug that is not delivered to the patient). In some examples, the manifold 100 can be configured symmetrically in T-connector or Y-connector configurations. In other examples, the manifold 100 can be configured asymmetrically as needed. The manifold 100 can be in a "flat 2D" orientation, in which all of the connection ports 120, 130, 140 are oriented within a 2D configuration, or the manifold 100 can be configured in a "3D" configuration where at least one connection port 120, 130, 140 is placed in a plane orthogonal to the plane of the remaining connection ports 120, 130, 140. In other examples, the manifold 100 can be configured to be rotated by user for ease of use and to prevent air from entering the infusion fluid path. The manifold 100 can be a sterile device for human use and can undergo sterilization methods such as ethylene oxide, gamma, or electron beam processes. The manifold 100 can be re-usable or can be a single use disposable item. One or more of the connection ports 120, 130, 140, for example on the inlet side, can contain a particulate matter filter, such as a 0.2-micron filter, for example to filter particulates out of the infusion drug or an air elimination filter to remove air introduced during the infusion fluid transfer process. The manifold 100 can be transparent, translucent, or opaque. The manifold 100 can be automatic, in that there is no interface on the device with which a user needs to interact to operate the manifold 100. In other examples, the manifold 100 can be configured to be manually activated using open-close valve mechanisms, such as stopcocks.

The unidirectional check valve luer connector allows the fluid to flow in a single direction. Similar devices that can be utilized include one-way valves, anti-siphon valves, or non-return valves. The connection ports 120, 130, 140 of the manifold 100 may operate based on pressure differential to prevent fluid from entering the unintended area and to avoid additional valve structure. To open the valve requires a higher pressure on the inlet side of the valve than on the outlet side of the valve. The valve will close when the outlet side has a higher pressure than the inlet side. This design prevents fluid from flowing back into the inlet side. In the context of the manifold 100, the inlet side is the connector side connected to the secondary delivery device 30, and the outlet side is the side connected to the neighboring primary delivery device 20 and ancillary device 40. When the secondary delivery device 30 is actuated, the inlet pressure increases and is greater than the outlet pressure side (given the infusion is not in progress), and thus the secondary connection port 130 can open and allow for flow. When the secondary delivery device 30 finishes dispensing, the outlet pressure is higher than the inlet pressure, and the valve closes, preventing flow back through the secondary connection port 130 and into the secondary prefilled delivery device 30 (e.g., syringe).

When the secondary delivery device 30 is actuated, the drug fluid travels primarily into the primary delivery device 20 and not to the infusion needle set of the ancillary device 40 because the primary delivery device 20 offers less fluidic resistance compared to the ancillary device 40. The primary delivery device 20 is a relatively large and open volume with little resistance to fluid flow whereas the ancillary device 40 can be comprised of long and narrow tubes that are intended to add resistance to the fluid path to slow the fluid. When the fluid leaves the secondary delivery device 30 as it is actuated, the fluid will travel the path of least resistance, that is, to the primary delivery device 20.

In an example of using the manifold 100, an infusion driving device 15 may be intended for use a specific primary delivery device 120, for example a 50 mL syringe. In an example scenario, a user may require an infusion therapy requiring 65 mL volume of drug that are received in a 50 mL and 15 mL pre-filled syringe. The 50 mL and 15 mL pre-filled syringes are of different volumes and size than the 50 mL primary delivery device 120 used with the infusion driving device 15, meaning that the infusion will not function as intended if the (different volume and size) pre-filled syringes were placed inside the infusion driving device 15. Instead of switching to another infusion pump system that accommodates the pre-filled syringes (which may not be immediately available, may be too expensive, or may require two systems to accommodate both pre-filled syringes), the user can use the infusion driving device 15 in combination with the manifold 100 disclosed herein. To carry out an infusion treatment, the user can perform the following steps:

A) Remove the cap for the primary connection port 120.
B) Connect the empty 50 mL primary delivery device 20 to the primary connection port 120.
C) Remove the cap for the secondary connection port 130.
D) Connect a 50 mL prefilled secondary delivery device 30 to the secondary connection port 130.
E) Actuate (press on) the secondary delivery device 30 to fill the primary delivery device 20.
F) Remove the cap for the delivery connection port 140.
G) Connect the infusion needle set of the ancillary device 40 to the delivery connection port 140.
H) Load the primary delivery device 20 into the infusion driving device 15.
I) Lock the primary delivery device 20 in place and arm the infusion driving device 15.
J) Begin the infusion.
K) When the first 50 mL is administered via the primary delivery device 20, release the safety tab on the infusion driving device 15.
L) Disconnect the 50 mL pre-filled secondary delivery device 30 on the secondary connection port 130.
M) Connect the 15 mL prefilled secondary delivery device 30 to the secondary connection port 130.
N) Actuate (press) on the secondary delivery device 30 to fill the primary delivery device 20.
O) Lock the primary delivery device 20 in place and arm the infusion driving device 15.
P) Continue the infusion.

The steps above highlight that the primary delivery device 20 does not once need to be removed or replaced throughout the infusion, reducing the need for additional labor in comparison to conventional syringe replacement methods. Also, the connection directly to the ancillary device 40 was not broken, reducing the risk for contamination when compared to syringe-to-syringe filling methods. Further, the user was able to use the manifold 100 with their infusion system 10 with secondary delivery devices 30 that were not physically compatible with their system, overcoming a limitation with conventional infusion pump systems.

In those instances where drug volumes in excess of a pre-filled 50 mL primary delivery device 20 are needed, the 50 mL primary delivery device 20 can be refilled when the initial volume infusion is completed. The 50 mL primary delivery device 20 can be refilled from a smaller pre-filled syringe, or any number of syringes of various types and sizes. After the 50 mL infusion, the pump is placed in its OFF position, which allows the infusion driving device 15 to be reset to accept additional drug volume when the primary delivery device 20 is refilled. The user then needs only to connect a new secondary delivery device 30 into the "T" Luer secondary connection port 130 on the manifold 100 and push. The actuation of the secondary delivery device 30 pushes back the syringe plunger of the primary delivery device 20. Accordingly, if a patient needed to receive 15 mL more, the user can connect a 10 mL syringe and a 5 mL syringe, respectively, and push them both into the primary delivery device 20 (actuate). When complete, the infusion driving device 15 is switched to back to OPERATE mode, and the lever on the infusion driving device 15 is pressed (readying the primary delivery device 20) until the infusion driving device 15 is fully charged.

For patients that need less than 50 mL or any volume, the same techniques can be used, the primary delivery device 20 (e.g., a 50 mL syringe) can be filled to the desired volume using multiple smaller secondary delivery devices 30 (e.g., syringes).

Figure 3:
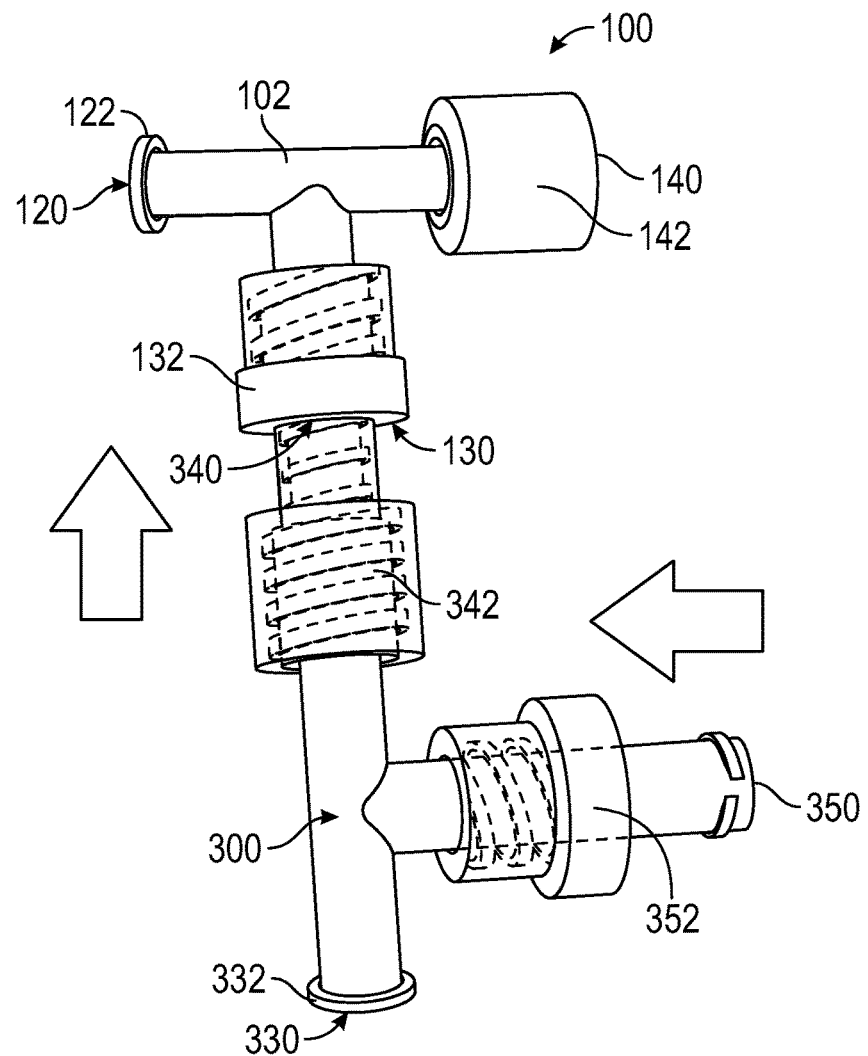
FIG. 3 is a manifold connected to an ancillary device of a second manifold.

FIG. 3 illustrates a manifold 100 that includes a second manifold 300 operable to provide fluid (e.g., a third infusion fluid, which can be the same as the first and/or the second infusion fluid) to refill the primary delivery device 20. In at least one example, the second manifold 300 can be substantially the same as the manifold 100. As illustrated in FIG. 3, the second manifold 300 is fluidly coupled with the manifold 100 such that fluid from the second manifold 300 is received in the manifold 100 to refill the primary delivery device 20 via the primary connection port 120.

The use of the second manifold 300 can be useful in situations where a third delivery device 400 is not compatible with the primary delivery device 20. There is no backflow in the system because of the connection ports 120, 130, 140, 330, 340, 350 and the relative pressures needed to open the respective connection ports 120, 130, 140, 330, 340, 350.

The second manifold 300 can include a first connection port 330 operable to be fluidly coupled with the second delivery device 30, a delivery connection port 340 in fluid communication with the first connection port 330 and operable to be in fluidly coupled with the secondary connection port 130 of the manifold 100, and a second connection port 350 operable to be fluidly coupled with the third delivery device 400. The second connection port 350 can be in fluid communication with the first connection port 330.

To reflect the example where the second manifold 300 is the same as the manifold 100, the first connection port 330 of the second manifold 300 can be the same as the primary connection port 120 of the manifold 100, the delivery connection port 340 can be the same as the delivery connection port 140 of the manifold 100, and the second connection port 350 can be the same as the secondary connection port 130 of the manifold 100. The features, properties, and/or functionalities for the ports 120, 130, 140 of the manifold 100 can apply to the corresponding ports 330, 340, 350 of the second manifold 300.

The fluid from the third delivery device 400 can be operable to flow: (1) from the secondary delivery device 30 through the first connection port 330 and through the delivery connection port 340 to the manifold 100 via the secondary connection port 130, and (2) from the third delivery device 400 through the second connection port 350 and through the first connection port 330 to be received by the secondary delivery device 30. Accordingly, the fluid from the third delivery device 400 refills the secondary delivery device 30. Then, the secondary delivery device 30 refills the primary delivery device 20. The primary delivery device 20 then delivers the fluid to the patient via the ancillary device 40.

FIGS. 4A-4G illustrate the manifold 100 connected to a second manifold 300 utilized in an infusion system 10 to replenish a primary delivery device 20 from a second delivery device 30 and a third delivery device 400.

Figure 4A:
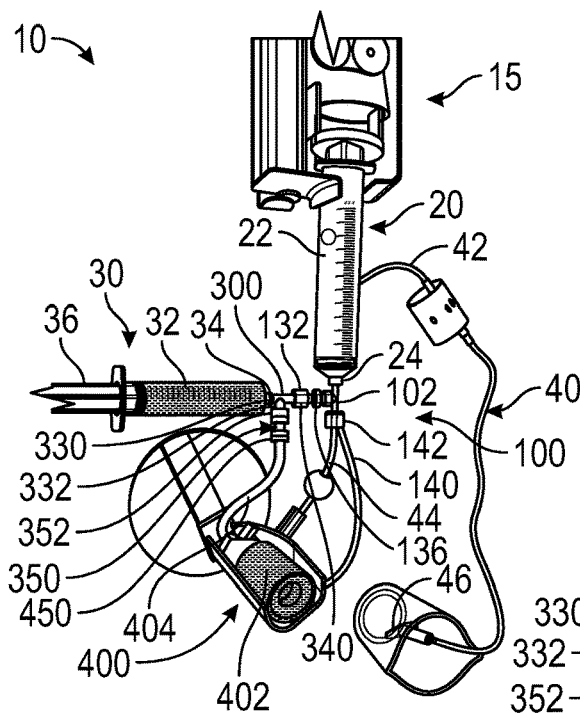
FIGS. 4A, 4B, 4C, 4D, 4E, 4F, and 4G are the manifold connected to a second manifold utilized in an infusion system to replenish a primary delivery device from a second delivery device and a third delivery device.

As shown in FIG. 4A, an empty primary delivery device 20 (e.g., a native pump syringe) is connected through the bi-directional primary connection port 120 of the manifold 100. A second manifold 300 is connected to the unidirectional secondary connection port 130 of the manifold 100 connected by the unidirectional delivery connector port 340 (e.g., male Luer) of the second manifold 300. A secondary delivery device 30 (e.g., prefilled secondary syringe) is connected to the bi-directional first connection port 330 of the second manifold 300. Similar to the discussion above, the delivery connection port 140 of the manifold 100 can be a unidirectional connection port that is connected to an ancillary device 40 (e.g., infusion needle set). A third delivery device 400 (e.g., a pre-filled vial) is also connected to a second connection port 350 that can be unidirectional of the second manifold 300. In at least one example, the user can connect the third delivery device 400 to the unidirectional second connection port 350 via connective tubing and/or a vial spike and invert the vial as shown in FIG. 4A.

Figure 4B:
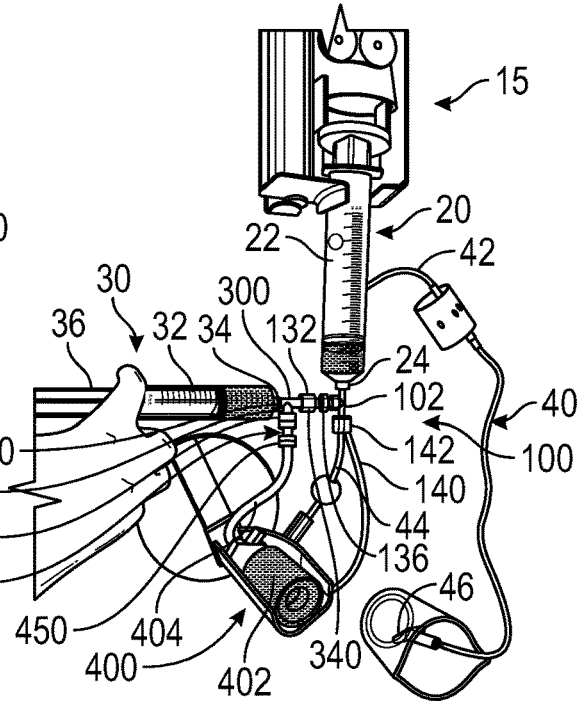
Figure 4C:
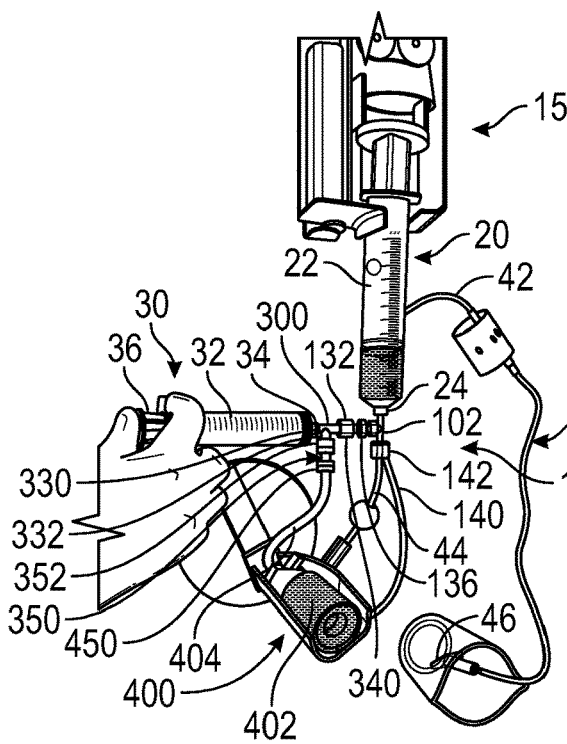

As shown in FIG. 4B, the user can actuate the secondary delivery device 30, and the pressure inside the secondary delivery device 30 becomes greater than the pressure in the primary delivery device 20, and the infusion fluid flows from the secondary delivery device 30 through the bidirectional first connection port 330 of the second manifold 300, through the unidirectional secondary connection port 130 of the first manifold 100, through the (bidirectional) primary connection port 120 and into the primary delivery device 20. FIG. 4C shows the empty secondary delivery device 30 after all the infusion fluid previously in the secondary delivery device 30 has been transferred to and received in the primary delivery device 20.

Figure 4D:
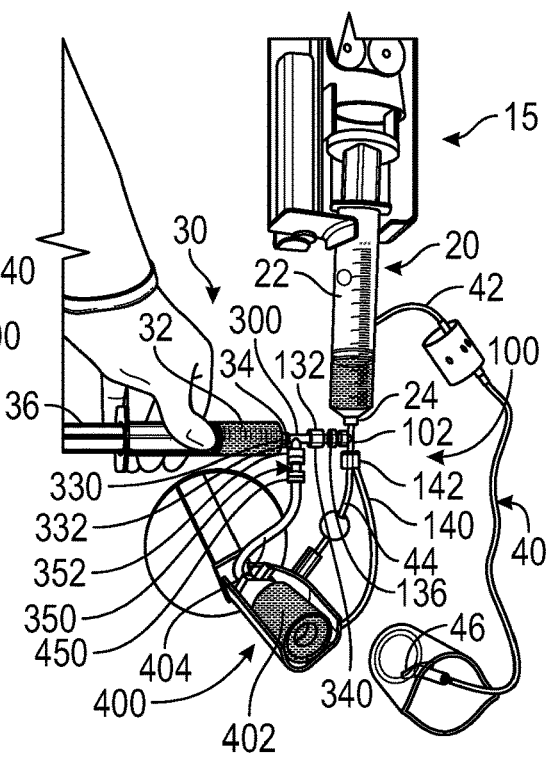
Figure 4E:
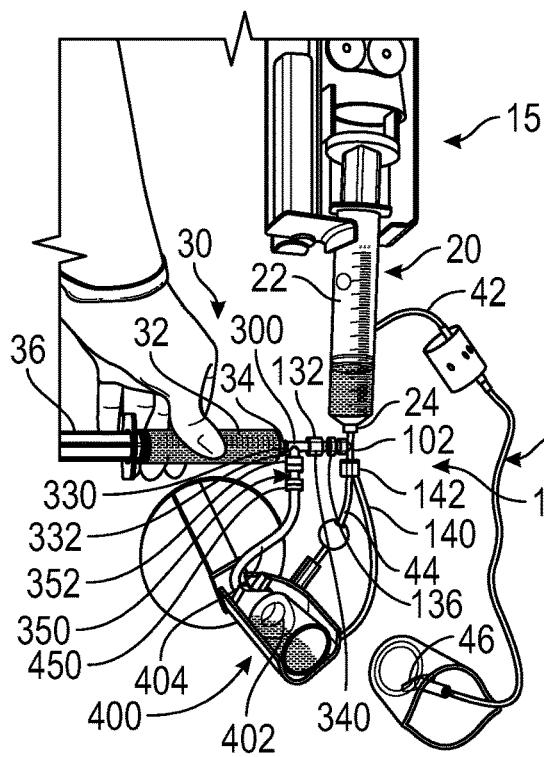

In FIG. 4D, the user can reverse the actuation of the secondary delivery device 30. In the example pictured in FIGS. 4D and 4E, the user can slowly pull the plunger 36 of the secondary syringe 30 (out). The pressure in the side of the secondary delivery device 30 of the second manifold 300 is now lower than the pressure inside the side of the second manifold 300 connected to the third delivery device 400 via the unidirectional second connection port 350, and the infusion fluid flows from the third delivery device 400 through the unidirectional second connection port 350 through the second manifold 300, through the (bidirectional) first connection port 330 and into the secondary delivery device 30. FIG. 2E shows the transfer from the third delivery device 400 to the second delivery device 30 when complete. That is, the secondary delivery device 30 is fully loaded as substantially all the infusion fluid from the third delivery device 400 has flowed into the secondary delivery device 30.

Figure 4F:
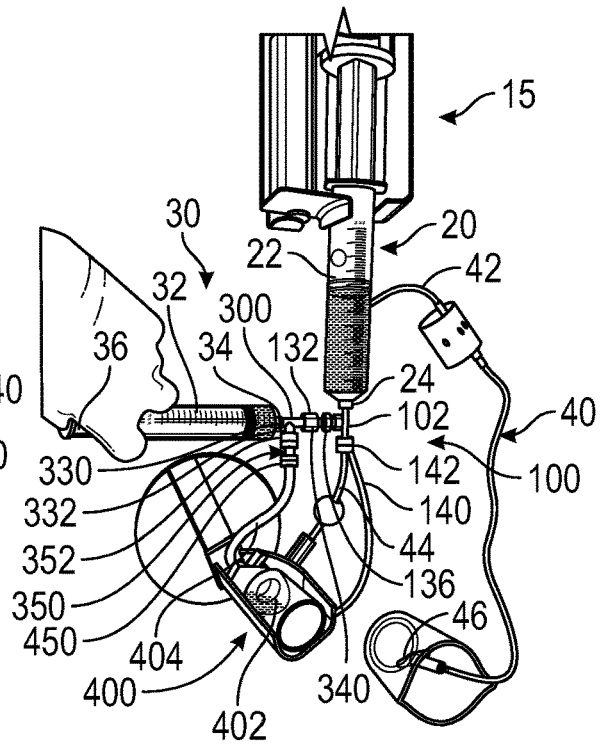
Figure 4G:
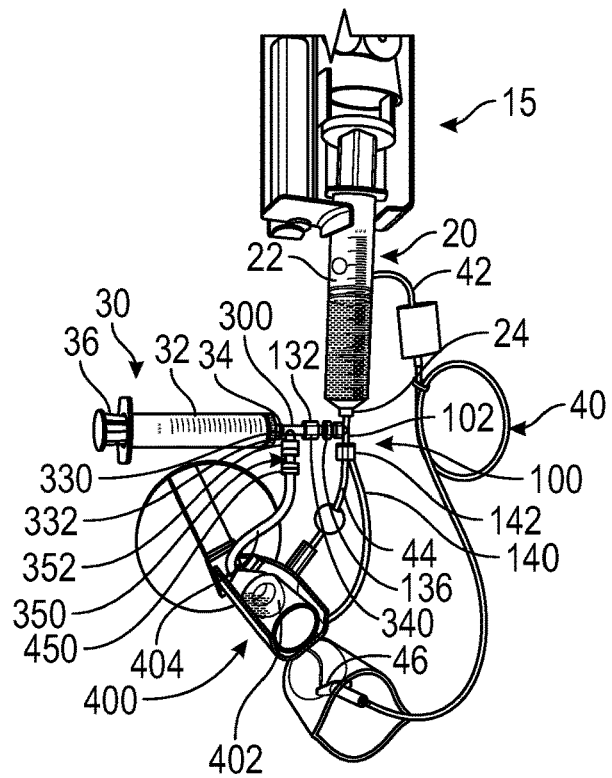

FIG. 4F shows the secondary delivery device 30 being actuated, and as the pressure on the side of the secondary delivery device 30 becomes greater than the pressure on the side of the primary delivery device 20, the infusion fluid again flows from the secondary delivery device 30 through the unidirectional secondary connection port 130 of the first manifold 100, through the body 102 of the first manifold 100, through the bidirectional primary connection port 120, and into the primary delivery device 20. If any air is inadvertently drawn into the infusion system 10, the air can be eliminated downstream by an in-line air filter connected before the infusion needle set 40. Once substantially all the infusion fluid is again transferred from the secondary delivery device 30 into the primary delivery device 20, the infusion driving device 15 can be loaded and reinitiate the infusion treatment. As shown in FIG. 4G, the infusion driving device 15 applies pressure to the primary delivery device 20, and infusion fluid flows from the primary delivery device 20 through the bidirectional primary connection port 120, through the body 102 of the manifold 100, through the unidirectional delivery connection port 140, optionally through the in-line air filter, and into the infusion needle set of the ancillary device 40. In the example illustrated in FIGS. 4A-4G, the infusion fluid is delivered to a beaker by the infusion needle set 40 rather than to a patient.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. An infusion system comprising:
a primary delivery device;
a secondary delivery device;
an ancillary device; and
a first manifold including:
a primary connection port operable to be fluidly coupled with the primary delivery device;
a delivery connection port in fluid communication with the primary connection port, the delivery connection port being operable to be fluidly coupled with the ancillary device, the delivery connection port being operable to permit unidirectional flow from the primary connection port to the ancillary device;
a secondary connection port operable to be fluidly coupled with the secondary delivery device, the secondary connection port being in fluid communication with the primary connection port, the secondary connection port being operable to permit unidirectional flow from the secondary delivery device to the primary connection port,
wherein the primary connection port is operable to permit bidirectional flow so that fluid is operable to flow: (1) from the primary delivery device through the primary connection port and through the delivery connection port to the ancillary device, and (2) from the secondary delivery device through the secondary connection port and through the primary connection port to be received by the primary delivery device;
a second manifold operable to be fluidly coupled with the secondary port of the first manifold, the second manifold including:
a first connection port operable to be fluidly coupled with the secondary delivery device;
a delivery connection port of the second manifold in fluid communication with the first connection port, the delivery connection port of the second manifold being operable to be fluidly coupled with the secondary connection port of the first manifold, the delivery connection port of the second manifold being operable to permit unidirectional flow from the first connection port to the secondary connection port of the first manifold;

a second connection port operable to be fluidly coupled with a third delivery device, the second connection port being in fluid communication with the first connection port, the second connection port being operable to permit unidirectional flow from the third delivery device to the first connection port, wherein the first connection port is operable to permit bidirectional flow so that fluid is operable to flow: (1) from the secondary delivery device through the first connection port and through the delivery connection port of the second manifold to the first manifold via the second connection port, and (2) from the third delivery device through the second connection port and through the first connection port to be received by the secondary delivery device.

2. The system of claim 1, wherein the primary delivery device includes a primary reservoir containing a first infusion fluid, wherein the first infusion fluid is operable to be delivered to the ancillary device.

3. The system of claim 1, wherein the secondary delivery device includes a secondary reservoir containing a second infusion fluid, wherein the second infusion fluid is operable to flow from the secondary delivery device through the secondary connection port and through the primary connection port to be received in a first reservoir of the primary delivery device.

4. The system of claim 3, wherein the primary delivery device is operable to deliver the second infusion fluid to the ancillary device by causing the second infusion fluid to flow from the primary delivery device through the primary connection port and through the delivery connection port to the ancillary device while the second infusion fluid is prevented from flowing through the secondary connection port.

5. The system of claim 3, wherein the second infusion fluid is operable to flow from the second connection port to the primary delivery device via the primary connection port while the second infusion fluid is prevented from flowing through the delivery connection port.

6. The system of claim 1, wherein the secondary connection port and/or the delivery connection port includes a check valve.

7. The system of claim 1, wherein the primary connection port includes a female luer connector operable to receive a male luer fitting on the primary delivery device.

8. The system of claim 1, wherein the secondary connection port includes a female luer connector operable to receive a male luer fitting on the secondary delivery device.

9. The system of claim 1, wherein the delivery connection port includes a male luer connector operable to be received by a female luer fitting on the ancillary device.

10. The system of claim 1, wherein the ancillary device includes an infusion needle set.

11. The system of claim 1, wherein the primary delivery device and/or the secondary delivery device includes a syringe.

12. A manifold system for infusion systems comprising:
a first manifold including:
  a primary connection port operable to be fluidly coupled with a primary delivery device;
  a delivery connection port in fluid communication with the primary connection port, the delivery connection port being operable to be fluidly coupled with an ancillary device, the delivery connection port being operable to permit unidirectional flow from the primary connection port to the ancillary device;
  a secondary connection port operable to be fluidly coupled with a secondary delivery device, the secondary connection port being in fluid communication with the primary connection port, the secondary connection port being operable to permit unidirectional flow from the secondary delivery device to the primary connection port,
  wherein the primary connection port is operable to permit bidirectional flow so that fluid is operable to flow: (1) from the primary delivery device through the primary connection port and through the delivery connection port to the ancillary device, and (2) from the secondary delivery device through the secondary connection port and through the primary connection port to be received by the primary delivery device; and
a second manifold operable to be fluidly coupled with the secondary connection port of the first manifold, the second manifold including:
  a first connection port operable to be fluidly coupled with the secondary delivery device;
  a delivery connection port of the second manifold in fluid communication with the first connection port, the delivery connection port of the second manifold being operable to be fluidly coupled with the secondary connection port of the first manifold, the delivery connection port of the second manifold being operable to permit unidirectional flow from the first connection port to the secondary connection port of the first manifold;
  a second connection port operable to be fluidly coupled with a third delivery device, the second connection port being in fluid communication with the first connection port, the second connection port being operable to permit unidirectional flow from the third delivery device to the first connection port,
wherein the first connection port is operable to permit bidirectional flow so that fluid is operable to flow: (1) from the secondary delivery device through the first connection port and through the delivery connection port of the second manifold to the first manifold via the second connection port, and (2) from the third delivery device through the second connection port and through the first connection port to be received by the secondary delivery device.

* * * * *